United States Patent [19]

Wright et al.

[11] 4,108,873

[45] Aug. 22, 1978

[54] O-(CARBOXYMETHYL)-4-CHROMANONE OXIME

[75] Inventors: George C. Wright; Marvin M. Goldenberg, both of Norwich, N.Y.

[73] Assignee: Morton-Norwich Products, Inc., Norwich, N.Y.

[21] Appl. No.: 812,103

[22] Filed: Jul. 1, 1977

[51] Int. Cl.$^2$ .......................................... C07D 311/04
[52] U.S. Cl. .................................. 260/345.2; 424/283
[58] Field of Search ..................................... 260/345.2

[56] References Cited

U.S. PATENT DOCUMENTS 3,706,764   12/1972   Nakanishi et al. ................ 260/345.2

*Primary Examiner*—Nicky Chan
*Attorney, Agent, or Firm*—Anthony J. Franze

[57] ABSTRACT

The compound O-(carboxymethyl)-4-chromanone oxime is useful as a gastric antisecretory agent.

1 Claim, No Drawings

O-(CARBOXYMETHYL)-4-CHROMANONE OXIME

This invention is concerned with the chemical compound O-(carboxymethyl)-4-chromanone oxime. This compound possesses pharmacological activity. In particular, it elicits gastric antisecretory effects when administered to animals. Thus, when dosed perorally to rats at a level of about 100 mg/kg in suitable pharmaceutical vehicle about one hour prior to pylorus ligation of the rat's stomach an inhibition of about 55% of gastric acid output is evoked and a reduction of volume of gastric secretions to the extent of about 42% is achieved.

This compound can be readily formulated in various pharmaceutical dosage forms such as tablets, elixirs, suspensions, capsules and the like using common-place carriers and excipients of the pharmaceutical art with which there is no incompatibility.

In order for this invention to be readily available to those skilled in the art, its currently preferred method of preparation is descirbed:

O-(Carboxymethyl)-4-chromanone Oxime

To a solution of N-(carboxymethoxy) amine ½ HCl (20.0 g., 0.18 mole) in 10% NaOH (54 ml., 0.14 mole) was added rapidly a solution of 4-chromanone (24.0 g., 0.16 mole) in ethanol (50 ml.), using rapid stirring. The reaction mixture was refluxed on the steam bath for 2 ¾ hrs., and stored in the refrigerator overnight. The resultant white solid was collected and washed well with isopropanol, ether and dried in air overnight, yield: 31 g. To the crude product in $H_2O$ (100 ml.) was added 10% HCl (20 ml) to a pH of 1-2, cooling in an ice bath and using hand stirring. The mixture was allowed to stand 0.5 hr., and the product was collected and washed well with $H_2O$, isopropanol, ether, m.p. 140°-142°. The product weighed 27 g. (85%), dried in a vacuum desiccator for 7 weeks.

Anal. Calcd. for $C_{11}H_{11}NO_4 \cdot \frac{1}{4}H_2O$: C, 58.53; H, 5.14; N, 6.21. Found: C, 58.90; H, 4.92; N, 6.08.

What is claimed is:

1. The compound O-(carboxymethyl)-4-chromanone oxime.